United States Patent [19]

Griffiths

[11] Patent Number: 4,961,502
[45] Date of Patent: Oct. 9, 1990

[54] REUSABLE STERILE X-RAY CASSETTE HOLDER

[76] Inventor: Gerald R. Griffiths, 1113 S. 71st St., West Allis, Wis. 53214

[21] Appl. No.: 311,129

[22] Filed: Feb. 15, 1989

Related U.S. Application Data

[63] Continuation-in-part of Ser. No. 146,306, Jan. 21, 1988, abandoned.

[51] Int. Cl.$^5$ ............................................. B65D 81/18
[52] U.S. Cl. .................................... 206/455; 220/334; 250/475.2; 378/167
[58] Field of Search ................ 206/455, 456; 220/334; 250/472.1, 475.2, 482; 378/167, 174, 177, 178, 180–182, 184, 204

[56] References Cited

U.S. PATENT DOCUMENTS

| | | | |
|---|---|---|---|
| 3,155,269 | 11/1964 | Schurman et al. | 220/334 |
| 3,394,838 | 7/1968 | Larkin | 220/326 |
| 3,710,977 | 1/1973 | Van den Enden et al. | 206/455 |
| 3,829,699 | 8/1974 | Anspach, Jr. | 378/167 |
| 3,843,041 | 10/1974 | Oliverius | 206/455 |
| 4,057,731 | 11/1977 | Loseff | 378/167 |
| 4,413,734 | 11/1983 | Newcombe, Jr. | 206/455 |
| 4,471,881 | 9/1984 | Foster | 220/334 |

FOREIGN PATENT DOCUMENTS

| | | | |
|---|---|---|---|
| 0149072 | 11/1936 | Austria | 220/334 |
| 0575104 | 2/1946 | United Kingdom | 206/455 |

OTHER PUBLICATIONS

"Protect-A-Grid", Advertisement, X-Ray Cassette Repair Company, 2 Sheets, 5-1986.
"Multi-Purpose Container", W. L. Wolf, Jr., Research Disclosure, 14859, 8-1976.

*Primary Examiner*—Jimmy G. Foster
*Attorney, Agent, or Firm*—James L. Kirschnik

[57] ABSTRACT

An X-ray cassette holding which is capable of being sterilized for use in an Operating Room includes a hinged cover and an opening for receiving a non-sterile X-ray cassette. A receiver portion into which the cassette is inserted is spaced from the interior of the side and end walls of a pivoting cover to isolate the exterior of the cassette holder from contamination by virtue of the insertion of a contaminated cassette into the holder. Seals may be provided to seal the cover edges and portions of the receiver edges from the exterior of the holder when the cover is in a closed position. When the cover is opened, the cassette may be removed, and a new cassette inserted without contaminating the exterior sterile surfaces of the holder.

21 Claims, 3 Drawing Sheets

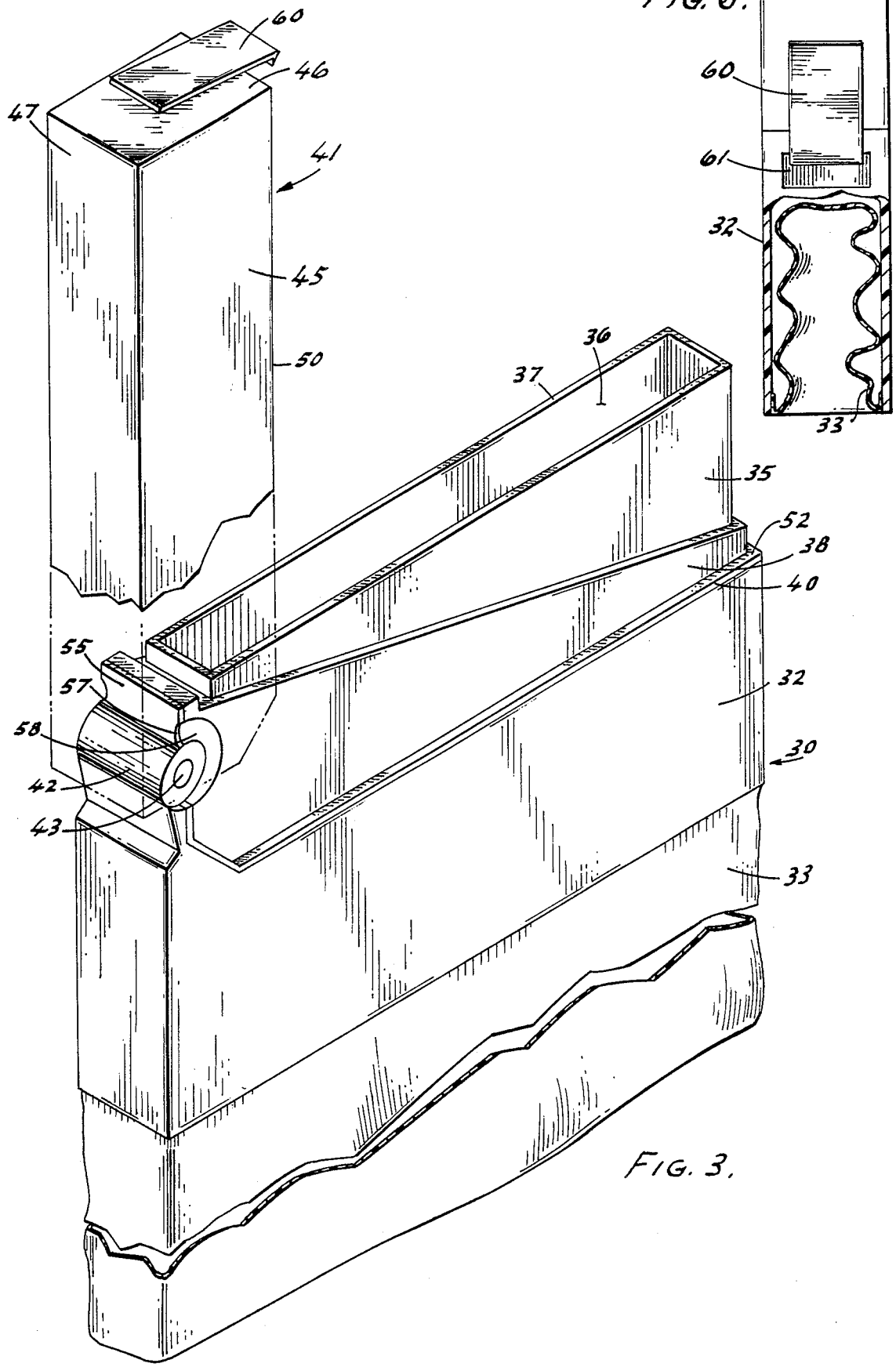

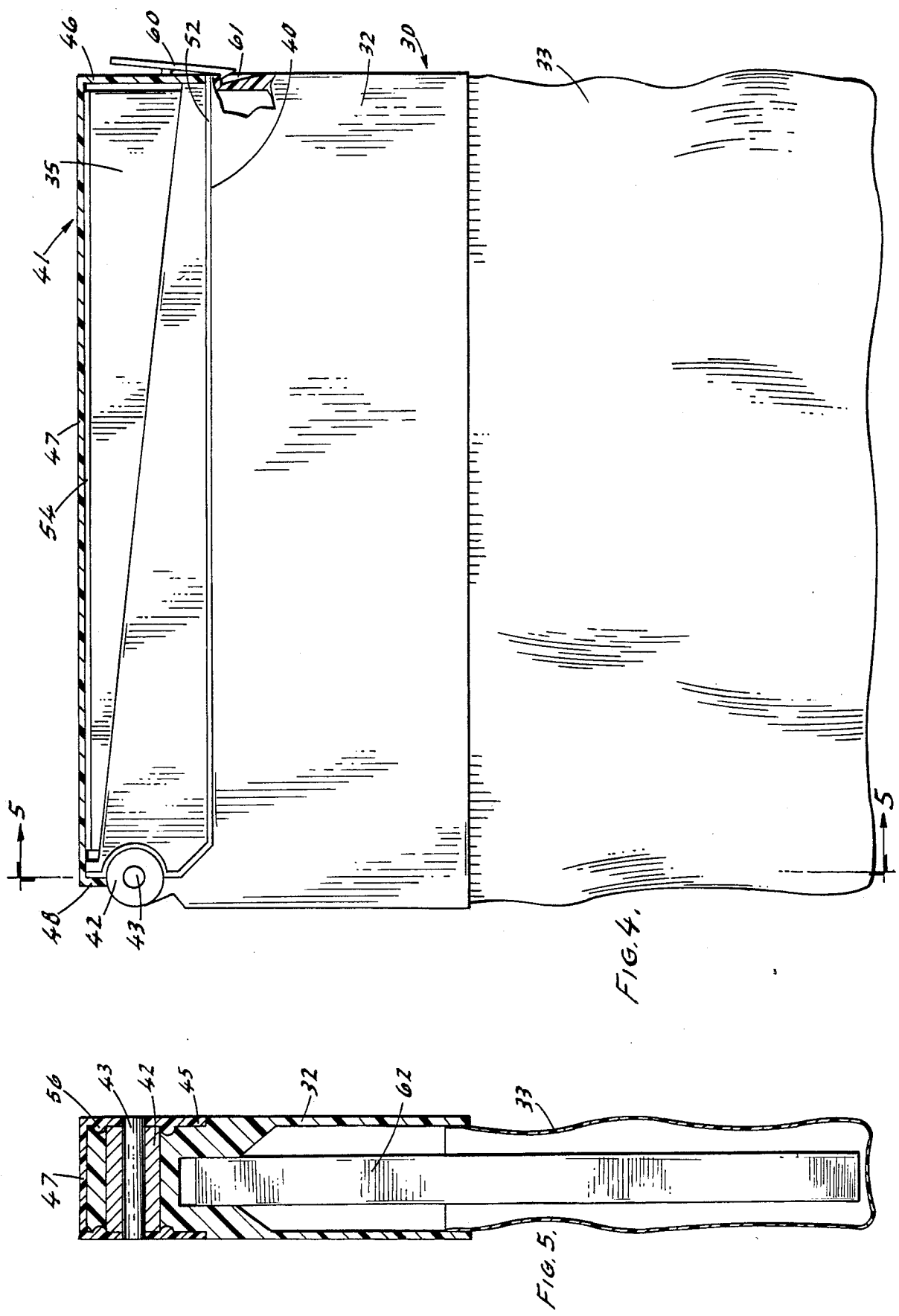

REUSABLE STERILE X-RAY CASSETTE HOLDER

CROSS-REFERENCE TO RELATED APPLICATION

This is a continuation-in-part of application Ser. No. 146,306 filed Jan. 21, 1988 now abandoned.

BACKGROUND OF THE INVENTION

1. Field Of The Invention

The present invention relates to sterile X-ray cassette holders for providing a sterile container for X-ray cassettes. The invention is directed to use in situations where X-rays are required to be taken during surgical operative procedures and the contaminated or non-sterile X-ray cassette must be isolated from the operative field.

2. Description Of The Prior Art

At the present time, various efforts have been made to provide sterile containers for X-ray cassettes for use in taking X-rays during operative prodedures. One such device used at the present time is described in U.S. Pat. No. 3,843,041 to Oliverius issued Oct. 22, 1974. The Oliverius device comprises a flexible sterile bag into which an X-ray cassette may be inserted. Since X-ray cassettes are generally not subject to economically effective sterilization, the non-sterile cassettes are typically inserted by a non-sterile technician into the sterile container which is held by a sterile member of the operating team. Once inserted, the Oliverius bag is closed to isolate the cassette so that an X-ray may be taken while a patient is on the operating table. Following the X-ray, the bag with the cassette inside is passed out of the operative field where the cassette may be removed and developed.

A disadvantage of this technique and configuration of the container is that the cassette container may only be used once as reopening the bag to remove the cassette cannot be reliably done without subjecting the container exterior to contamination. Furthermore, the bag-like container is often contaminated with the blood of a patient and these contaminants may be potential health hazards to the personnel who must remove the X-ray cassette for development. In addition, disposal of the contaminated bag outside the operating area is necessary since a patient's blood may contain extremely infectious or hazardous pathogens. Obvious dangers from bacteria exist as to non-operating personnel who may not be as well protected as the operating team. Airborne migration of pathogens from the bag is also a potential problem.

Another type of sterile cassette holder is shown in U.S. Pat. No. 3,829,699 to Anspach issued Aug. 13, 1974. The Anspach device comprises a transparent cassette container with a flexible hinge and cover that seals the top of the container after the cassette is in place. Although the Anspach device has certain advantages over the Oliverius bag type holder, such as the ability to more effectively seal the container and avoid airborne contaminants, the Anspach holder does not lend itself to permitting more than one X-ray being taken with the device as contamination of the lip of the opening of the container when the X-ray cassette is inserted is likely.

SUMMARY OF THE INVENTION

It is an object of the present invention to provide a sterile container for X-ray cassettes which permits insertion and removal of cassettes without contaminating the exposed sterile portions of the container which may come in contact with a patient in an operating room.

A further object of the invention is to provide a cassette holder for X-ray cassettes which may be utilized for a series of X-rays without danger of contamination.

Another object of the invention is to provide a container for X-ray cassettes which permits removal of the cassette while in the Operating Room and retention of the holder for additional X-rays and later disposal from within the Operating Room itself.

The present invention comprises a container for X-ray cassettes which includes a hinged cover affixed to a cassette receiving portion which includes an opening for receiving an X-ray cassette. A cover guide may be provided for maintaining the cover in a spaced relationship from the receiving portion of the container to avoid contamination of the cover by the interior or exposed edges having contacted the X-ray cassette. The container may include a flexible bag-like portion for containing a portion of the cassette or an entirely rigid container may be provided. A bactericidal seal may be provided to seal the cover when closed to further isolate the interior of the container from the passage of airborne contaminants from within the container. Other objects and advantages of the invention will become apparent from a description of a preferred embodiment which follows.

DESCRIPTION OF THE DRAWINGS

FIG. 3 is a perspective view of an alternate and preferred embodiment of an X-ray cassette holder according to the invention;

FIG. 4 is a side elevation view of the cassette holder shown in FIG. 3 with the side of the cover removed;

FIG. 5 is a section view taken along line 5—5 of FIG. 4; and,

FIG. 6 is an end view in partial section of a cassette holder as shown in FIG. 3 configured for shipment and storage prior to use.

DESCRIPTION OF A PREFERRED EMBODIMENT

Figure 1:
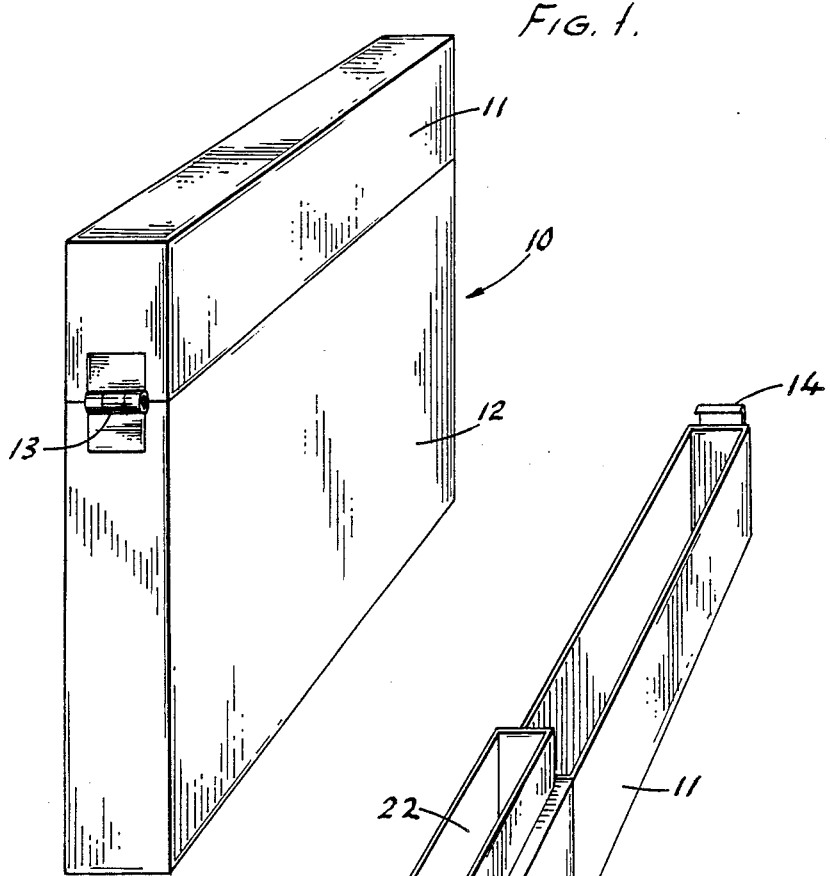
FIG. 1 is a perspective view of an X-ray cassette holder according to one version of the invention.
Figure 2:
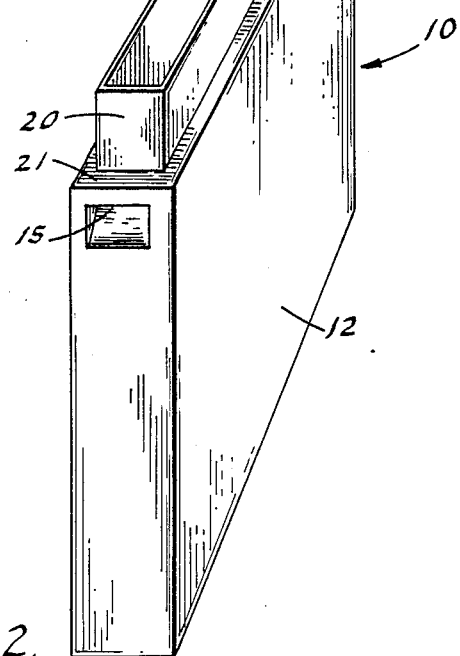
FIG. 2 is a reverse perspective of the X-ray cassette holder shown in FIG. 1 with the cover open.

Referring to FIGS. 1 and 2, an X-ray cassette holder as described in my original application is shown. The cassette holder 10 is in the shape of a hollow right rectangular prism defined by a cover 11 and main body portion 12. The cover 11 is attached at one end by a hinge 13 to the body 12 and has a resilient tab type latch 14 at its opposite end for engaging a locking recess 15 formed in the opposite end of the body 12 when the cover is in a closed position. As seen in FIG. 2, with the cover 11 open, the body 12 has a cassette receiver portion 20 at its exposed upper end which is of a reduced rectangular cross section compared to that of cover 11 and the body 12. A ridge 21 couples the receiver 20 to the upper end of the body 12, and the receiver 20 has an open top portion 22 for receiving an X-ray cassette. The hinge 13 is relatively rigid so as to not permit lateral movement of the cover 11, and the side and end walls of the cover 11 are spaced from the periphery of the receiver portion 20 when the cover is in a closed position. As previously disclosed, the components of the cassette holder 10 in this embodiment are preferably formed from rigid moisture resistant material such as laminated cardboard or plastic, as long as the materials are capable of sterilization by conventional methods such as irradiation. In practice, a sterile operating person can manually open the cover 11 to expose the receiver 20 for receiving an X-ray cassette, not shown with a non-sterile person handling the cassette. Once the cassette is in place within the container body 12, the cover would be closed by the sterile operating room personnel and by virtue of keeping the receiver 20 spaced from the interior of the cover 11, any contamination on the edges of the receiver 20 at the opening 22 will not contact the cover 11. After an X-ray is taken, a sterile operating room person simply reverses the procedure to open the cover and permit removal of the cassette and insertion of a new cassette by a non-sterile person if desired. As long as the non-sterile person removing the cassette avoids contact with the sterile exposed portions of the cassette holder 10 and the sterile operating room personnel avoid contact with the contaminated edge of the receiver 20, repeat X-rays may be taken with little danger of contamination passing or being exposed to the patient within the operating room.

A preferred embodiment of the invention is shown in FIGS. 3 through 6 where a cassette holder 30 according to the invention includes a rigid upper collar portion 32 and a downwardly extending flexible bag-like bottom portion 33. The collar 32 includes a central upstanding receiver portion 35 which is generally rectangular in shape and hollow with an upper opening 36 communicating with the interior of the collar and bag 33 for receiving X-ray cassettes. Receiver 35 has a top edge 37, and surrounding the periphery of three sides of receiver 35 is a cover guide 38 whose uppermost portions are spaced downwardly from the top edge 37 and whose lowermost portions terminate at a generally horizontal ridge 40 extending around the entire collar 32. A pivotable cover 41 is attached to an upstanding hinge post 42 located at one end of the collar 32 and spaced from the end of receiver 35. A hinge pin 43 passes through both the cover 41 and hinge post 42 which permits the cover 41 to pivot open and shut. Cover 41 includes side walls 45 and an end wall 46 and a top portion 47 and hinge end wall 48.

As is seen in FIGS. 4 and 5, when the cover 41 is pivoted to a closed position, its bottom edge 50 will rest along the ridge 40 with the cover side walls 45 and end wall 46 spaced from the receiver 35. A resilient seal material 52 may be included between ridge 40 and cover edge 50, and the cover guide 38 insures that as the cover is pivoted, the side walls 45 will always remain spaced from the sides of receiver 35. Additionally, a resilient seal material 54 may be provided between the upper edge 37 of the receiver 35 and the interior portion of the cover top 47 to effectively seal off the interior of the cassette holder from the exterior with the cover 41 in a closed position.

To aid in sealing at the pivot point, the interior of end wall 48 may also engage a resilient seal 55 attached to the back of the hinge post 42 when the cover 41 is closed. Additionally at the hinge pivot juncture, an arcuate protuberant portion 56 on the interior of the cover engages a similarly shaped arcuate depression 57 formed in the hinge post and which may also have a resilient bed of seal material 58.

As in the first described embodiment, a latch 60 is attached to the swinging end of the cover and engages a recess 61 formed in the collar 32 for locking the cover 41 in a closed position. In practice, a preferred seal material for the resilient seals described heretofore is an antimicrobial protein activated bactericidal material such as manufactured by the 3 M Company under the trademark "IOBAN". This material not only aids in sealing the joints with the cover 41 closed, but also acts to kill any bacteria which might result from contact between the contaminated cassette upon insertion or removal and the receiver.

As seen in FIG. 5, a cassette 62 is shown inserted within the bag 33 and collar 32 with the cover 41 in a closed position. As is readily apparent, the non-sterile cassette 62 is entirely confined within the interior of the cassette holder 30 and thereby isolated totally from the exterior. In practice, the cassette holder 30 would be sterilized and available within an operating room for use as needed. Conventional sterilization techniques such as irradiation could be utilized to sterilize the holder 30 before use. When X-rays are necessary, a sterile operating room person would simply take the cassette holder 30 and open the cover 41. A non-sterile cassette 62 may then be manually loaded through the opening 36 of the receiver 35 and inserted into the holder 30. Since the receiver 35 and its upper edge 37 are spaced from the sides of the cover 41, any contamination of the opening 36 or edge 37 will not go beyond that point. Such contamination would be further impeded by the use of a bactericidal seal material described previously. Removal of the cassette is accomplished by the sterile operating room person opening the cover 41 whereby the cassette 62 may be removed from the holder 30 by pushing on the bottom of bag 33 to move the cassette 62 upward for manual removal. The reverse procedure would be followed for inserting a new cassette. At the conclusion of the operating room procedures, the holder 30 having been retained in the operating room, is simply discarded with other contaminated operating room debris and hazards to non-operating room personnel who handle the X-ray cassettes are thereby minimized as well.

FIG. 6 shows a partial cross sectional end view of a cassette holder 30 with the bag portion 33 folded and inserted within the confines of the collar 32 to illustrate the minimal amount of space taken up by the assembled unit for shipping and storage purposes. The components of the invention are preferably made of inexpensive material such as molded plastics so long as they permit forming a sealed connection between the bag 33 and collar 32 with the bag 33 also being formed from a flexible plastic material capable of sterilization.

While a preferred embodiment of the invention as thus been described, those skilled in the art will appreciate the fact that variations in the configuration, materials suggested or other changes may be possible without departing from the scope or intent of the invention which is to be taken solely from an interpretation of the claims which follow.

What is claimed is:

1. An X-ray cassette holder for receiving non-sterile X-ray cassettes during operative procedures comprising:
   a. hollow enclosure means for containing a non-sterile X-ray cassette and having an open end;
   b. rigid collar means affixed to the open end of said enclosure means and having an upstanding open receiver portion for receiving and guiding said X-ray cassette during insertion into said enclosure means, said receiver portion including side and end walls inwardly spaced from the perimeter of said collar means;

c. said collar means having a peripheral ridge extending generally transversely between said collar perimeter and said receiver side and end walls;

d. cover means attached to said collar means and pivotable on a hinge between an open position exposing said receiver means and a closed position for sealing said container and its contents with the cover in a closed position and for permitting the removal or insertion of a non-sterile X-ray cassette when said cover is in an open position;

e. said cover means including side and end walls and a top and having its internal surfaces spaced from said receiver portion during opening and closing of said cover means and when said cover means is closed, said cover means engaging said ridge in its closed position to seal the interior of the holder from the exterior;

f. said hinge being adapted to prevent lateral movement of said cover means relative to said receiver portion for minimizing contamination from said non-sterile cassette; and, g. said enclosure means, collar means and cover means being formed of materials which are capable of being sterilized and which also permit exposure of an X-ray cassette contained therein to X-rays.

2. A device as set forth in claim 1, wherein said enclosure means comprises a flexible plastic sheet material with its open end sealed around said collar means.

3. A device as set forth in claim 2, wherein said cover means includes releasable latch means for locking said cover in a closed position on said collar means.

4. A device as set forth in claim 3, including resilient seal means for sealing the interior of said device from the exterior when said cover means is in a closed position.

5. A device as set forth in claim 1, wherein said cover means includes releasable latch means for locking said cover in a closed position on said collar means.

6. A device as set forth in claim 1, including resilient seal means for sealing the interior of said device from the exterior when said cover is in a closed position.

7. A device for receiving non-sterile articles comprising:

a. hollow enclosure means for containing a non-sterile article and having an open end;

b. rigid collar means affixed to the open end of said enclosure means and having an open receiver portion for receiving said non-sterile article during insertion into said enclosure means;

c. cover means attached to said collar means and pivotable on a hinge between an open position exposing said receiver means and a closed position for sealing said container and its contents with the cover in a closed position and for permitting the removal or insertion of a non-sterile article when said cover is in an open position;

d. said cover means including side and end walls spaced from said receiver portion when said cover means is closed;

e. said hinge being adapted to prevent lateral movement of said cover means relative to said collar means;

f. said enclosure means, collar means and cover means being formed of materials which are capable of being sterilized;

g. said receiver means having a reduced cross sectional area relative to the cross sectional area of said collar means;

h. said enclosure means comprising a flexible plastic sheet material with its open end sealed around said collar means;

i. said cover means including releasable latch means for locking said cover in a closed position on said collar means;

j. resilient seal means for sealing the interior of said device from the exterior when said cover means is in a closed position; and, k. said seal means comprising a bactericidal material.

8. A device for receiving non-sterile articles comprising:

a. hollow enclosure means for containing a non-sterile article and having an open end;

b. rigid collar means affixed to the open end of said enclosure means and having an open receiver portion for receiving said non-sterile article during insertion into said enclosure means;

c. cover means attached to said collar means and pivotable on a hinge between an open position exposing said receiver means and a closed position for sealing said container and its contents with the cover in a closed position and for permitting removal or insertion of a non-sterile article when said cover is in an open position;

d. said cover means including side and end walls spaced from said receiver portion when said cover means is closed;

e. said hinge being adapted to prevent lateral movement of said cover means relative to said collar means;

f. said enclosure means, collar means and cover means being formed of materials which are capable of being sterilized; and, g. resilient seal means for sealing the interior of said device from the exterior when said cover is in a closed position, said seal means comprising a bactericidal material.

9. A sterile container for X-ray cassettes comprising:

a. a hollow bottom enclosure having sealed sides, a sealed bottom and an open top portion;

b. said open top portion being affixed to a rigid collar, said collar including receiving means having an opening formed therein for permitting and guiding the insertion of an X-ray cassette through said collar into said enclosure, said receiver means including side and end walls spaced inwardly from the outer perimeter of said collar;

c. said collar means having a peripheral ridge extending generally transversely between said collar perimeter and said receiver side and end walls;

d. a pivotable cover attached to said collar and pivotable between an open position and a closed position, said cover being adapted to seal the interior of said container from the exterior when said cover is in a closed position;

e. said cover including side and end walls and a top portion, the interior surfaces of said cover means being spaced from said receiver means during opening and closing and when said cover means is in a closed position, said cover side and end walls engaging said ridge to seal the enclosure when said cover is in its closed position; and, f. said cover being pivotable on hinge means for limiting lateral motion of said cover relative to collar.

10. A device as set forth in claim 9, wherein said bottom enclosure comprises a flexible plastic sheet material.

11. A device as set forth in claim 10, wherein said cover includes releasable latch means for locking said cover in a closed position.

12. A device as set forth in claim 11, including resilient seal means for sealing the interior of said container from the exterior when said cover is in a closed position.

13. A device as set forth in claim 9, wherein said cover includes releasable latch means for locking said cover in a closed position.

14. A device as set forth in claim 9, including resilient seal means for sealing the interior of said container from the exterior when said cover is in a closed position.

15. A sterile container for X-ray cassettes comprising:
 a. a hollow bottom enclosure having sealed sides, a sealed bottom and an open top portion;
 b. said open top portion being affixed to a rigid collar, said collar including receiver means having an opening formed therein for permitting the insertion of an X-ray cassette through said collar into said enclosure;
 c. a pivotable cover attached to said collar and pivotable between an open position and a closed position, said cover being adapted to seal the interior of said container from the exterior when said cover is in a closed position;
 d. said cover including side and end walls and a top portion, the interior of said cover means being spaced from said receiver means when said cover means is in a closed position;
 e. said cover being pivotable on hinge means for limiting lateral motion of said cover relative to said collar;
 f. said bottom enclosure comprising a flexible plastic sheet material;
 g. said cover including releasable latch means for locking said cover in a closed position; and,
 h. resilient seal means for sealing the interior of said container from the exterior once the cover is in a closed position, said seal means comprising a bactericidal material.

16. A device as set forth in claim 15, wherein said receiver means having a reduced cross-sectional area in comparison to the cross-sectional area of said collar means.

17. A sterile container for X-ray cassettes comprising:
 a. a hollow bottom enclosure having sealed sides, a sealed bottom and an open top portion;
 b. said open top portion being affixed to a rigid collar, said collar including receiver means having an opening formed therein for permitting the insertion of an X-ray cassette through said collar into said enclosure;
 c. a pivotable cover attached to said collar and pivotable between an open position and a closed position, said cover being adapted to seal the interior of said container from the exterior when said cover is in a closed position;
 d. said cover including side and end walls and a top portion, the interior of said cover means being spaced from said receiver means when said cover means is in a closed position;
 e. said cover being pivotable on hinge means for limiting lateral motion of said cover relative to said collar;
 f. resilient seal means for sealing the interior of said container from the exterior when said cover is in a closed position, said seal means comprising a bactericidal material.

18. A device as set forth in claim 17, wherein said receiver means having a reduced cross-sectional area in comparison to the cross-sectional area of said collar.

19. A device as set forth in claim 18, including guide means for maintaining said cover side walls in a spaced relationship with said receiver means.

20. The combination of an X-ray cassette and an X-ray cassette holder adapted to permit removal and insertion of the cassette during an operative procedure, wherein said cassette holder comprises:
 a. hollow enclosure means for containing said cassette and having an open end;
 b. rigid collar means affixed to the open end of said enclosure and having a generally transversely inwardly extending ridge at its upper portion and coupled to an upstanding receiver portion having side and end walls and surrounding a portion of said X-ray cassette;
 c. pivotable cover means attached to said collar means and pivotable on a hinge to move between an open position exposing said receiver and cassette, and a closed position for sealing said container in a closed position; and,
 d. said cover means including side and end walls and a top portion, said side and end walls and top portion being spaced from said receiver means during opening and closing of the cover and in its closed position, said cover side and end walls engaging said ridge in its closed position to seal said container.

21. A device as set forth in claim 20 wherein said enclosure means comprises a flexible plastic sheet material having its open end sealed around said collar means.

* * * * *